(12) United States Patent
Mendius et al.

(10) Patent No.: US 9,320,526 B1
(45) Date of Patent: Apr. 26, 2016

(54) PUNCTUM PLUG

(71) Applicant: Enteroptyx, Memphis, TN (US)

(72) Inventors: Richard W. Mendius, Collierville, TN (US); Robert Wade Allen, Memphis, TN (US); Patrick Ireland, Cordova, TN (US)

(73) Assignee: ENTEROPTYX, Memphis, TN (US)

( * ) Notice: Subject to any disclaimer, the term of this patent is extended or adjusted under 35 U.S.C. 154(b) by 570 days.

(21) Appl. No.: 13/649,426

(22) Filed: Oct. 11, 2012

Related U.S. Application Data

(60) Provisional application No. 61/546,572, filed on Oct. 13, 2011.

(51) Int. Cl.
| | |
|---|---|
| *A61F 5/37* | (2006.01) |
| *A61F 13/00* | (2006.01) |
| *A61F 11/00* | (2006.01) |
| *A61F 9/00* | (2006.01) |
| *A61B 19/00* | (2006.01) |
| *A61B 17/00* | (2006.01) |
| *A61M 5/00* | (2006.01) |
| *A61M 5/31* | (2006.01) |
| *A61M 25/00* | (2006.01) |
| *A61M 35/00* | (2006.01) |

(Continued)

(52) U.S. Cl.
CPC ............ *A61B 17/12159* (2013.01); *A61B 17/00* (2013.01); *A61B 17/0057* (2013.01); *A61B 17/064* (2013.01); *A61B 17/0644* (2013.01); *A61B 17/12* (2013.01); *A61B 17/12131* (2013.01); *A61F 6/00* (2013.01); *A61F 6/14* (2013.01); *A61F 6/146* (2013.01); *A61F 6/20* (2013.01); *A61F 9/00* (2013.01); *A61F 9/007* (2013.01); *A61F 9/00781* (2013.01); *A61K 9/00* (2013.01); *A61K 9/0048* (2013.01); *A61K 9/0051* (2013.01)

(58) Field of Classification Search
CPC .. A61B 17/00; A61B 17/0057; A61B 17/064; A61B 17/0644; A61B 17/0645; A61B 17/12159; A61B 17/12131; A61B 17/12; A61F 6/00; A61F 6/14; A61F 6/146; A61F 6/20; A61F 9/00; A61F 9/007; A61F 9/00772; A61K 9/00; A61K 9/0048; A61K 9/0051
USPC ......... 128/846, 869, 887, 830, 831, 843, 857, 128/858; 604/8–10, 241, 294, 295, 298, 604/93.01, 104, 264, 278; 606/107, 191, 606/193, 196, 197, 199; 137/15.24, 384
See application file for complete search history.

(56) References Cited

U.S. PATENT DOCUMENTS 4,631,051 A * 12/1986 Harris ............................... 604/9
4,936,825 A *  6/1990 Ungerleider ..................... 604/8

(Continued)

*Primary Examiner* — Alireza Nia
*Assistant Examiner* — Brandon L Jackson
(74) *Attorney, Agent, or Firm* — Gordon & Jacobson, P.C.

(57) ABSTRACT

A punctum plug includes a proximal head, a shaft, and a distal body, and an axial bore. The head is defined by a flexible circular flange with a convex upper portion and a concave lower portion. The body defines a frustoconically tapered distal tip and a two wings that extend in an arc and taper in thickness. The wings can extend further radially than the flange of the head. A recessed groove is defined around the shaft extending between the wings and a wall structure connecting the winged portions of the body. The above structure permits one plug or fewer plugs to accommodate a broad patient population.

18 Claims, 1 Drawing Sheet

(51) Int. Cl.
  *A61B 17/12* (2006.01)
  *A61F 6/14* (2006.01)
  *A61F 6/20* (2006.01)
  *A61K 9/00* (2006.01)
  *A61F 9/007* (2006.01)
  *A61B 17/064* (2006.01)
  *A61F 6/00* (2006.01)

(56) References Cited

U.S. PATENT DOCUMENTS

| | | | |
|---|---|---|---|
| 4,959,048 A * | 9/1990 | Seder et al. | 604/9 |
| 5,283,063 A * | 2/1994 | Freeman | 424/427 |
| 5,334,137 A * | 8/1994 | Freeman | 604/8 |
| 5,513,659 A * | 5/1996 | Buuck et al. | 128/885 |
| 5,723,005 A | 3/1998 | Herrick | |
| 5,830,171 A * | 11/1998 | Wallace | 604/8 |
| 6,041,785 A * | 3/2000 | Webb | 128/887 |
| 6,149,684 A | 11/2000 | Herrick | |
| 6,306,114 B1 | 10/2001 | Freeman et al. | |
| 6,629,533 B1 | 10/2003 | Webb et al. | |
| 7,017,580 B2 | 3/2006 | Prescott et al. | |
| 7,204,253 B2 * | 4/2007 | Mendius | A61B 17/0057 128/846 |
| 7,862,832 B2 * | 1/2011 | Moe et al. | 424/464 |
| 8,439,819 B2 * | 5/2013 | Shalon et al. | 600/32 |
| 8,439,865 B2 * | 5/2013 | Lust et al. | 604/93.01 |
| 2007/0083146 A1 | 4/2007 | Murray | |
| 2007/0298075 A1 * | 12/2007 | Borgia et al. | 424/428 |

* cited by examiner

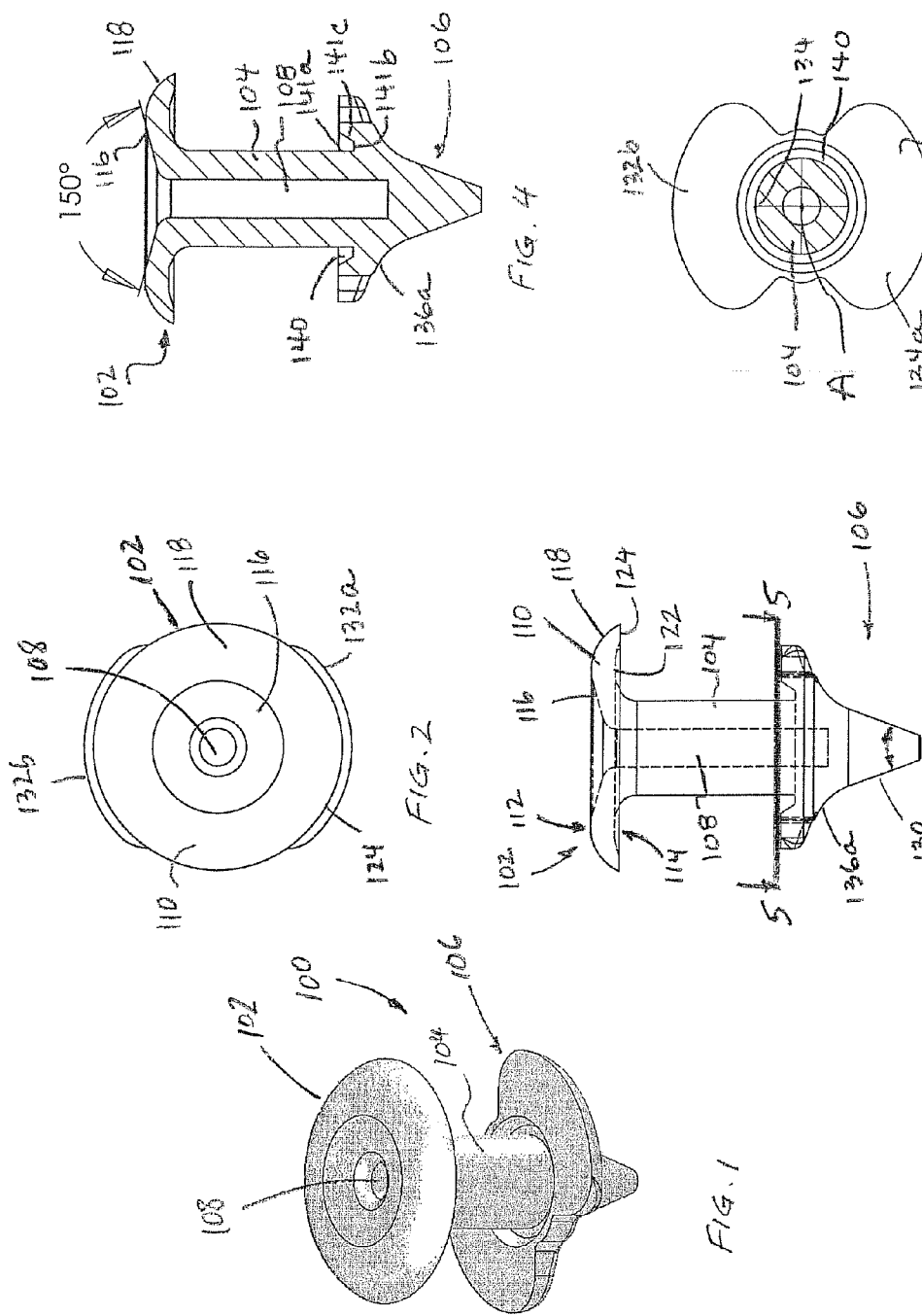

PUNCTUM PLUG

BACKGROUND OF THE INVENTION

1. Field of the Invention

The present invention relates broadly to prostheses. More particularly, this invention relates to ophthalmologic prostheses, and even more particularly to punctum plugs.

2. State of the Art

The surface of the eye and the inner surface of the eyelid are lubricated by tear fluid constantly produced by glands around the eye. A tiny hole, known as the lacrimal punctum, located at the medial margin of each of the upper and lower lid margins drains the tear fluid away into the nasal lacrimal ducts.

A variety of eye problems are related to an insufficient volume of lubrication at the surface of the eyes. The most common is keratoconjunctivitis sicca, also known as dry eye syndrome. A common cause for the insufficient tear volume is the drainage of too great a volume of tear fluid through the punctal opening, the lacrimal duct, and into the nasal passage, thereby removing the tear fluid from where it is needed at the eye surface. Contact lens wearers particularly suffer when there is insufficient tear fluid volume at the ocular surface. In addition, dry eye is a component of various ocular diseases such as corneal ulcers, conjunctivitis, pterygium, blepharitis, keratitis, red lid margins, recurrent corneal erosion, filamentary keratitis and other external eye conditions.

A number of methods for closing the punctal opening have been used to retain tear fluid at the eye surface to prevent or alleviate dry eye syndrome, including suturing, laser sealing, and plugging. Plugging with a punctum plug is the least severe solution, is relatively inexpensive, and is being performed with increasing frequency.

In addition, punctum plugs may be useful in decreasing contact lens intolerance, for increasing retention/enhancement of ocular medications on the eye, for maintenance of ocular flora, for punctal stenosis, and to enhance healing and comfort after surgery.

A punctum plug typically includes an elongate shaft having a proximal end and a distal end, a head at the proximal end of the shaft, and a relatively larger body at the distal end of the shaft for occluding the lacrimal punctum. The plug is usually provided with a proximal axial bore for receiving a removable insertion tool.

In the current punctum plug insertion procedure, the sphincter muscle about the punctal opening is dilated with a dilator and an insertion tool, on which the plug is mounted, is used to maneuver the plug towards the dilated punctum. Force is then applied to the insertion tool to move the body of the plug through the punctal opening, the muscles of the punctal ring, and into the vertical punctum of the lacrimal canaliculus until the plug is fully inserted. The plug is fully inserted when the head seats against the tissue at the punctal opening and the body seats within the lacrimal punctum and vertical canaliculus so as to block the passage of tear fluid into the punctum and thereby retain tear fluid at the surface of the eye. Once the plug is fully inserted in the punctum, the insertion tool is decoupled from the plug and withdrawn.

Plugs are generally provided in several sizes to accommodate different sizes of lacrimal punctum so that the plug will achieve a good fit. That is, the plug should block drainage of tear fluid for a given patient's punctum size, the plug should fit stably within the punctum and not be subject to inadvertent release, and the plug should be relatively comfortable for the patient. For example, punctal dilation tends to permit plugs that are too large for a particular punctum to be inserted therein. Then, once the punctal opening reassumes its natural size, the plug may cause irritation to the recipient. In addition, the stress of a plug too large for the particular punctum may undesirably permanently stretch the punctal anatomy. In addition, it is not uncommon for plugs to be inserted into a punctum that are too small for that punctum, and such plug then being prematurely extruded, often within days of implantation. Therefore, it is necessary for the treatment provider to stock a range of size of plugs so that the correct size can be implanted in the patient.

SUMMARY OF THE INVENTION

A punctum plug includes a proximal head, a shaft, and a distal body. A longitudinal axis is defined through the plug, and an axial bore is defined through the head, at least a portion of the shaft, and preferably also a portion of the body.

The head is defined by a flexible flange that extends outward from the shaft 360° about the shaft, such flange most preferably being circular in shape. The flange includes an upper surface and a lower surface. The upper surface includes a conical central portion and a curved convex outer portion, each of which extends 360° in rotation about the shaft. The lower surface includes has a concave portion and a relatively flat peripheral edge, each of which extends 360° in rotation about the shaft. The peripheral edge extends distally of the concave portion. The flange defines a spring-like cap that seats on the lid margin and cups the annulus of the punctal opening. The large flexible flange seats low on the lid margin and comfortably retains the plug in place, preventing the plug from migrating down into the canaliculus. Further, the flexibility of the flange and its ability to deform as necessary maintains such low profile over a range of lid margin sizes.

The body defines a frustoconically tapered distal tip. Proximal the tip, the body flares outward into two tapered wings, each extending circumferentially through an arc. The upper surfaces of the wings preferably extend in a plane oriented transverse to the longitudinal axis. The wings preferably extend further radially than the flange of the head. A recessed groove is defined in the body and around the shaft extending between the wings and a wall structure connecting the winged portions of the body. This accommodates collapse of the wings proximally toward the head. When forced into a punctal opening, the wings fold against the shaft to fit a broader range of anatomy. Once the wings have been advanced to the vertical punctum, the wings open outward to secure the plug and prevent inadvertent extraction.

The above structure permits one plug or fewer plugs to effectively accommodate, in both treatment and comfort, a greater range of patient population than previous plugs. The plug is extremely well-tolerated by patients. In addition, fewer plugs need to be stocked in a care facility. Further aspects of the invention will become apparent to those skilled in the art upon reference to the detailed description taken in conjunction with the provided figures.

BRIEF DESCRIPTION OF THE DRAWINGS

FIG. 1 is a perspective view of a punctum plug according to the invention.

FIG. 2 is a top view of the punctum plug of FIG. 1.

FIG. 3 is a transparent side view of the punctum plug of FIG. 1.

FIG. 4 is a longitudinal section view of the punctum plug of FIG. 1.

FIG. 5 is a cross-section view of the punctum plug of FIG. 1, taken across line 5-5 in FIG. 3.

DETAILED DESCRIPTION OF THE PREFERRED EMBODIMENTS

Referring to FIGS. 1 through 6, a punctum plug 100 according to the invention is shown. The punctum plug 100 includes a shaft 104 with proximal and distal ends, a head 102 at the proximal end of the shaft, a body 106 at the distal end of the shaft 104. A longitudinal axis A extends through the plug, and an axial bore 108 is defined into the head 102, at least a portion of the shaft 104, and preferably also a portion of the body 106.

Referring to FIGS. 2 through 4, the head 102 is defined by a flexible flange 110 that extends 360° in rotation about the shaft 104. The flange 110 is most preferably circular in shape. The flange 110 includes an upper surface 112 and a lower surface 114. The upper surface 112 includes a central conical portion 116 preferably having an included angle of 150°±15°, and an outer convexly curved portion 118. The lower surface 114 includes a concave portion 122 extending to a preferably flat peripheral edge 124, each of the concave portion 122 and the peripheral edge 124 extending 360° in rotation about the shaft 104. The peripheral edge 124 extends distally of the more central concave portion 122. The structure of the flange 110 imparts a resilient flexibility to the head 102 as it seats on a patient's lid margin. The relatively large flexible flange 110 is adapted to seat low on the lid margin with the concave portion 122 of the lower surface 114 cupping the anatomical structure at the punctal opening so that the head 102 rests very low on the lid margin. In addition, the low seating flange 110 prevents the plug 100 from causing a foreign body sensation that would otherwise result in discomfort to patients. The structure of the head 102, with one size and a common amount of material, accommodates both small and large puncta as well as sizes in between.

Referring to FIGS. 3 through 5, the body 106 defines a frustoconically tapered distal tip 130 having an included angle of 35° to 45°, and more preferably 40°±2°. Proximal the tip 130, the body flares outward into two tapered wings 132a, 132b, each extending in diametrically opposite directions and rotationally through an arc. In one embodiment, for wing 132a, the wing extends through an arc greater than 90° about the longitudinal axis A, and more preferably through an arc of 125°±20° about the longitudinal axis A. Another way of describing the arc of wing 132a is 90°±20° about a point 134 on the outer surface of the shaft 104 located diametrically opposite from the radial direction in which the wing 132a extends. As best seen in FIG. 2, wing 132a preferably extends further radially than the peripheral edge 124 of the flange 110 of the head 102. Wing 132a has an upper surface 134a preferably oriented in a plane transverse to, and more preferably orthogonal to, the longitudinal axis A, and a lower surface 136a that concavely curves from the tip 130 toward the edge 138a of the wing such that the wing 132a tapers in diameter. Wing 132b is structured in a like manner to wing 132a.

A circumferential groove 140 is defined in the body 106 completely around the shaft 104, and recessed relative to the planar upper surface 134a and a partially circumferential wall structure 142 extending between the wings 132a, 132b. As best seen in FIG. 4, the groove 140 is defined by a vertical inner wall 141a extending in common with the outer surface of the shaft 104, a flat lower surface 141b, and an inclined outer wall 141c. The groove 140 in the upper surface 134a of the body accommodates folding the wings 132a, 132b proximally toward the head 102. The groove 140 is preferably not recessed into the wall of the shaft 104 in order to prevent lateral weakening of the shaft. When forced into a punctal opening, the wings 132a, 132b collapse against the shaft 104 to fit a broader range of anatomy. Once the wings 132a, 132b have been advanced to the vertical punctum, the resilience of the wings forces the wings outward to secure the plug and prevent inadvertent extraction.

In accord with the above, the plug 100 is sized to be inserted into the punctum of a human eye and accommodated therein. As such the plug (100) has an overall length not exceeding 0.1 inch, a shaft (104) length not exceeding 0.05 inch, a wing (132a, 132b) diameter not exceeding 0.075 inch, and a head (102) diameter not exceeding 0.075 inch. By way of exemplar dimensions, in one embodiment, the plug (100) has an overall length of 0.071 inch, a shaft length of 0.035 inch, a body (102) length of 0.03 inch, a maximum wing (132a, 132b) diameter of 0.056 inch, a head (102) diameter of 0.052 inch, a shaft (104) outer diameter of 0.02 inch, and a bore (108) diameter of 0.008 inch. A plug of the exemplar dimension can be used within puncta of a broad range of sizes, including punctal openings of 0.02 inch-0.03 inch.

The plug 100 is preferably a unitary molded construct, made from silicone. The plug is preferably molded from silicone which has sufficient strength, resilience, and elasticity for the structure and function described above. However, other materials known in the art of punctum plugs and of suitable properties can be used.

There have been described and illustrated herein embodiments of a punctum plug. While particular embodiments of the invention have been described, it is not intended that the invention be limited thereto, as it is intended that the invention be as broad in scope as the art will allow and that the specification be read likewise. Thus, while particular aspects of a preferred embodiment have been disclosed, it will be appreciated that not all of the features described need be included within a particular embodiment, and that embodiments of the invention may include describe features of only the head or body. It will therefore be appreciated by those skilled in the art that yet other modifications could be made to the provided invention without deviating from its spirit and scope as claimed.

What is claimed is:

1. A punctum plug for insertion into a punctal opening of a human eye, comprising:
   a) a shaft portion having first and second ends and defining a longitudinal axis;
   b) a head portion at said first end of said shaft portion, said head portion defined by a flexible circular flange, said flange having an upper surface and a lower surface,
      said upper surface including a convex portion extending 360° in rotation about said shaft portion, and
      said lower surface including a concave portion extending to a peripheral edge, each of said concave portion and said peripheral edge extending 360° in rotation about said shaft portion, said peripheral edge extending distally of the concave portion,
      wherein an axial bore is defined into said head and at least a portion of said shaft; and
   c) a body portion coupled to said second end of said shaft portion, said body portion having a distally tapered tip and exactly two diametrically opposing wings proximal said tip, each said wing,
      i) formed as a circumferential extension that extends about an angle of greater than 90° in rotation about a periphery of the body portion, the angle centered about the longitudinal axis and oriented transverse to the longitudinal axis, ii) extending radially further at said periphery than said peripheral edge of said flange, and iii) a planar upper surface transverse to the longitudinal axis and a concave curving lower surface, such that said wing tapers toward said periphery, and said body portion defining a circumferential groove extending completely around the shaft portion, radially inward of said wings, and recessed below said planar upper surface of said wings such that resilient deformation of said wings toward said head portion is accommodated by said groove.

2. A punctum plug according to claim 1, wherein said upper surface of said head defines a conical portion central of said convex portion.

3. A punctum plug according to claim 2, wherein said conical portion is defined by an included angle of 150°±15° relative to said longitudinal axis.

4. A punctum plug according to claim 1, wherein said distal tip frustoconical.

5. A punctum plug according to claim 4, wherein said distal tip has an included angle of 35°-45° relative to said longitudinal axis.

6. A punctum plug according to claim 1, wherein said peripheral edge is flat.

7. A punctum plug according to claim 1, wherein each said wing extends 125°±20° about said longitudinal axis.

8. A punctum plug according to claim 1, wherein each said wing is also formed as a rotational extension of 90°±20° about a point on an outer surface of said shaft portion, said point located diametrically opposite from the radial direction in which the wing extends.

9. A punctum plug according to claim 1, wherein said body portion includes a partially circumferential wall structure extending between said wings and said groove extends between said wall structure and said shaft portion.

10. A punctum plug for insertion into a punctal opening of a human eye, comprising:
    a) a shaft portion having first and second ends and defining a longitudinal axis;
    b) a head portion at said first end of said shaft portion, said head portion defined by a flexible circular flange, said flange having an upper surface and a lower surface,
        said upper surface including a convex portion extending 360° in rotation about said shaft, and
        said lower surface including a concave portion extending to a peripheral edge, each of said concave portion and said peripheral edge extending 360° in rotation about said shaft portion, said peripheral edge extending distally of the concave portion,
        wherein an axial bore is defined into said head and at least a portion of said shaft portion; and
    c) a body portion coupled to said second end of said shaft portion, said body portion having a distally tapered tip and exactly two diametrically opposing wings proximal said tip, a planar upper surface, and a circumferential groove extending completely around the shaft, the groove defined entirely as a recess within and below said planar upper surface, wherein resilient deformation of said wings toward said head portion is accommodated by said groove.

11. A punctum plug according to claim 10, wherein said upper surface of said head defines a conical portion central of said convex portion.

12. A punctum plug according to claim 10, wherein said peripheral edge is flat.

13. A punctum plug according to claim 10, wherein each said wing is formed as a rotational extension of at least 90° about said longitudinal axis.

14. A punctum plug according to claim 10, wherein said planar upper surface is oriented transverse to the longitudinal axis.

15. A punctum plug according to claim 10, wherein said circumferential groove is located radially inward of said wings.

16. A punctum plug for insertion into a punctal opening of a human eye, comprising:
    a) a shaft portion having first and second ends and defining a longitudinal axis;
    b) a head portion at said first end of said shaft, said head portion defined by a flexible circular flange, said flange having an upper surface and a lower surface meeting at a peripheral edge,
        wherein an axial bore is defined through said head and at least a portion of said shaft; and
    c) a body portion coupled to said second end of said shaft portion, said body portion having a distally tapered tip and exactly two diametrically opposing wings proximal said tip, each said wing,
        i) formed as a circumferential extension that extends about an angle of 125°±20° in rotation about a periphery of the body portion, the angle centered about the longitudinal axis,
        ii) extending radially further at said periphery of said body than said peripheral edge of said flange, and
        iii) a planar upper surface oriented transverse to the longitudinal axis and a concave curving lower surface, such that said wing tapers toward said periphery, and said body portion defining a circumferential groove completely around the shaft portion and recessed below said planar upper surface such that resiliently deformation of said wings toward said head portion is accommodated by said groove.

17. A punctum plug according to claim 16, wherein each said wing is also formed as an extension of 90°±20° about a point on an outer surface of said shaft portion, said point located diametrically opposite from the radial direction in which the wing extends.

18. A punctum plug according to claim 16, wherein said body portion includes a partially circumferential wall structure extending between said wings and said groove extends between said wall structure and said shaft portion.

* * * * *